United States Patent [19]

Hay et al.

[11] Patent Number: 4,788,314

[45] Date of Patent: Nov. 29, 1988

[54] METHOD FOR PRODUCING POLYMERIZABLE MONOMERS CONTAINING A SULPHATE GROUP

[75] Inventors: John N. Hay, Woking; Ian G. Meldrum, Leatherhead, both of England

[73] Assignee: The British Petroleum Company p.l.c., London, England

[21] Appl. No.: 53,566

[22] Filed: May 21, 1987

Related U.S. Application Data

[63] Continuation of Ser. No. 854,884, Apr. 23, 1986, abandoned, which is a continuation of Ser. No. 510,837, Jul. 5, 1983, abandoned.

[30] Foreign Application Priority Data

Jul. 22, 1982 [GB] United Kingdom ............... 8221267

[51] Int. Cl.$^4$ ............................................. C07C 141/10
[52] U.S. Cl. ......................................... 558/32; 556/27; 556/139
[58] Field of Search ................... 558/32; 556/27, 139

[56] References Cited

U.S. PATENT DOCUMENTS 3,839,393  10/1974  Strecker ............................... 558/32
3,875,202  4/1975   Strecker ............................... 558/32

FOREIGN PATENT DOCUMENTS 55-11525  1/1980  Japan .

*Primary Examiner*—Nicky Chan
*Attorney, Agent, or Firm*—Morgan & Finnegan

[57] ABSTRACT

A method for producing sulphatoalkyl acrylates or methacrylates having the general formula;

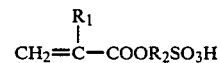

where $R_1$ is H or $CH_3$, $R_2$ is one or more alkoxylate groups each of which has from 1 to 4 carbon atoms, comprises reacting a hydroxy alkyl acrylate or methacrylate having the formula;

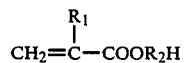

where $R_1$ and $R_2$ are as defined above, with chlorosulphonic acid at a temperature of less than 20° C. to form the acid ester. Salts of the acid ester may be produced by reaction with a basic metal salt, ammonium salt or quaternary ammonium salt.

10 Claims, No Drawings

METHOD FOR PRODUCING POLYMERIZABLE MONOMERS CONTAINING A SULPHATE GROUP

This is a continuation of co-pending application Ser. No. 854,884, filed on Apr. 23, 1986, now abandoned, which is a continuation of 510,837 filed July 5, 1983 (abandoned).

The present invention relates to a method for producing polymerizable monomers containing a sulphate group.

Polymerizable ammonium and alkali metal salts of sulphatoalkyl acrylates and methacrylates are known. U.S. Pat. No. 3,839,393 discloses such polymerizable sulphate-containing monomers and a method of preparing them, which method comprises condensing a hydroxyalkyl acrylate or methacrylate with sulphamic acid at a temperature in the range 90° C. to 120° C., in the presence of an organic amide as a catalyst and in the presence of a polymerization inhibitor.

Chlorosulphonic acid is known as a sulphating agent. However, it has surprisingly been found that sulphated alkyl acrylates and methacrylates can be produced at a relatively low temperature by reacting a hydroxyalkyl acrylate or methacrylate with chlorosulphonic acid. Indeed it has been found that by carrying out the reaction at a temperature of less than 20° C. the production of unwanted by-products can be minimised.

Thus according to the present invention a method for producing polymerizable monomers having the general formula;

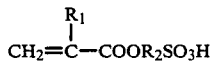

where
R₁ is a hydrogen atom or a methyl group
R₂ is one or more alkoxylate groups each of which alkoxylate group has from one to four carbon atoms, which method comprises the addition of a hydroxy alkyl acrylate or methacrylate having the formula;

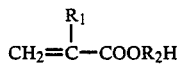

wherein R₁ and R₂ are the same as defined above, to chlorosulphonic acid wherein the reaction is carried out at a temperature in the range 0° to 10° C. and in which the reaction mixture is purged with a sparging gas.

Preferably the reaction is carried out at a temperature in the range −20° C. to 15° C., more preferably the temperature is in the range 0° to 10° C. At reaction temperatures above 20° C. the addition of hydrogen chloride across the double bond becomes significant and disproportionation of the hydroxy alkyl acrylate or methacrylate occurs.

The hydroxy alkyl acrylate or methacrylate used in the method of the present invention may contain more than one alkoxylate group. The alkoxylate groups may all be the same alkoxylate or they may be of two different alkoxylates e.g. the monomer may contain both ethoxylate and propoxylate groups. Such a mixture of alkoxylate groups may impart surface active properties to the monomer or to a polymer containing the monomer. Also, the alkoxylate groups may increase the tolerance of the monomer or a polymer containing the monomer to polyvalent metals such as for example magnesium, calcium, strontium and barium.

Suitable hydroxylated monomers which may be sulphated by the method include, 2-hydroxyethyl methacrylate, 2-hydroxypropyl methacrylate, 2-hydroxyethyl acrylate and ethoxylated and propoxylated derivatives of these methacrylates or acrylate. The hydroxy alkyl acrylates or methacrylates may be prepared by conventional methods such as, for example, the reaction between alkylene oxide and acrylic or methacrylic acid. The product is usually a mixture of hydroxy alkyl acrylates or methacrylates, unused methacrylic or acrylic acid and minor amounts of by-products. For example, 2-hydroxyethyl methacrylate produced in this way typically comprises 94% wt 2-hydroxyethyl methacrylate, 5% of ethoxylated hydroxyethyl methacrylate and 0.56% ethylene glycol dimethacrylate, the balance being unused methacrylic acid and naphtha.

The reaction between the hydroxy alkyl acrylate or methacrylate and the chlorosulphonic acid produces the acid ester. The invention includes neutralising the acid ester with a basic salt to give a sulphatoalkyl acrylate or methacrylate salt having the general formula;

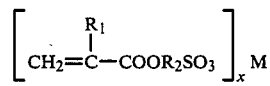

Where
R₁ and R₂ are as defined above
M is a metal ion, an ammonium ion or a quaternary ammonium ion and
X is an integer being equal to the valency of M It should be noted that "basic salt" as used in this specification includes oxide, hydroxide, carbonate and bicarbonate salts.

Ammonium and alkali metal salts of sulphatoalkylene acrylates and methacrylates are known. However, by neutralising the acid ester produced according to the present invention polyvalent metal salts may be produced. The invention therefore includes a polymerizable monomer having the general formula;

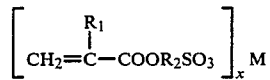

Where
R₁, R₂ and x are as defined above, and
M is a polyvalent metal ion

Suitable monovalent ions for M are ions of alkali metals particularly potassium and sodium ions. A particularly suitable basic salt is potassium carbonate. Suitable polyvalent metal ions include the ions of the alkaline earth metals, aluminum and iron.

The acid ester may be neutralized by reaction with a basic metal salt, an ammonium salt or a quaternary amonium salt. The basic salt may be a salt having the required ion M. Alternatively any convenient basic salt may be used to neutralise the acid ester and then the required ion M may be introduced into the monomer by for example ion exchange. The ion-exchange reaction may, for example, be carried out by passing the neutralized monomer solution over an organic ion exchange resin containing the required ion M. Any of the conventional ion-exchange resins may be used e.g. divinyl benzene-styrene copolymers. Such resins are commercially available under the registered trade marks of, for example, Amberlite, Dowex and Zerolit. References in this specification to neutralising the acid ester with a basic salt are to be taken to include both the direct and indirect method of introducing the required ion M.

The neutralization is also preferably carried out at a temperature below 20° C. More preferably the temperature is in the range 0° to 10° C.

Preferably the neutralization of the acid ester is carried out in the presence of a polymerization inhibitor. Any conventional inhibitor may be used such as, for example, p-methoxyphenol or cuprous chloride.

P-methoxyphenol is only effective in the presence of oxygen and so if this polymerization inhibitor is used the mixture is preferably purged with an oxygen containing gas such as air. Oxygen is itself a polymerization inhibitor and so an air purge could be used even if p-methoxyphenol is not present as an inhibitor. A polymerization inhibitor can also be used during the reaction between the chlorosulphonic acid and hydroxyalky acrylate or methacrylate.

The monomers according to the present invention may be polymerised by conventional methods such as, for example, free radical polymerization. The monomers may be co-polymerised with other monomers such as, for example, N,vinylpyrrolidene, methacrylamidopropyltrimethylammonium chloride, styrene, vinyl acetate, acrylamide or other acrylates or methacrylates including hydroxy ethyl methacrylate and phosphated hydroxy ethyl methacrylate.

The sulphate group is highly hydrophilic and so monomers according to the present invention may be copolymerised with other monomers which have an affinity for a non-aqueous phase in order to produce surface active polymers. Such polymers may be useful as emulsifiers in for example paints, cutting fluids and hydraulic oils. If the co-monomer has a strong affinity for a solid, the polymer may be adsorbed onto the surface effectively covering the surface with sulphate groups which attract water. These polymers would attract water in preference to other material and so may find uses as sacrificial agents in enhanced oil recovery to prevent the loss of surfactant by adsorption or they may be sprayed onto beaches prior to the arrival of an oil slick which would increase the hydrophilicity of the sand and rocks thereby assisting the eventual removal of oil. Polymers containing the sulphated monomers produced according to the method may also be useful as dispersant, detergent builders or scale inhibitors.

The invention is illustrated with reference to the following examples.

EXAMPLE 1

23.3 g (0.2 mol) of chlorosulphonic acid were placed in a three-neck flask fitted with a dropping funnel, a mechanical stirrer and an inlet for nitrogen. The flask was cooled to below 5° C. in an ice bath and 26 g (0.2 mol) of hydroxyethyl methacrylate were added dropwise over a period of about 30 minutes while maintaining the reaction mixture at a temperature below 10° C. The viscous solution was stirred for a further 30 minutes. The ice bath was then removed and the flask purged with nitrogen for 30 minutes to remove dissolved hydrogen chloride. The solution was added to a mixture of 13.8 g (0.1 mol) of potassium carbonate and 60 g of ice, maintaining the temperature below 5° C. The pH of the solution was adjusted to 10 by the addition of solid potassium carbonate. 160 cm$^3$ of isopropanol and 100 cm$^3$ of distilled water were added to the solution producing a white precipitate which was separated by filtration and the filtrate washed with petroleum ether. Freeze drying in the absence of light produced a fine white powder.

The yield was about 50 percent and the $^1$H and $^{13}$C N.M.R. spectrum confirmed that the product was sulphated hydroxyethyl methacrylate.

EXAMPLE 2

46.6 g (0.4 mol) of chlorosulphonic acid were placed in a flask and cooled in an ice bath to below 5° C. with stirring and air sparging. 53.1 g (0.408 mol) of 2-hydroxyethyl methacrylate were added dropwise over a period of about 2 hours, maintaining the temperature below 5° C. The product was neutralized by adding it dropwise over a period of about 20 minutes to a mixture of 27.6 g (0.2 mol) potassium carbonate, 120 g ice, 40 ml distilled water. The mixture also contained 0.08 g p-methoxyphenol as polymerization inhibitor. The mixture was purged with air throughout the neutralization and the temperature was maintained below 5° C. After all of the acid ester had been added to the basic salt solution, the pH was adjusted to about 7 by the addition of further potassium carbonate. The product was filtered and the solution extracted with hexane to remove dimethacrylate. The remaining solution contained 26% by weight of 2-sulphatoethyl methacrylate.

EXAMPLE 3

The following method of preparing 2-sulphatoethyl methacrylate was repeated at various temperatures.

52.1 g (0.4 mol) of 2-hydroxyethyl methacrylate were added dropwise to 46.6 g (0.4 mol) of chlorosulphonic acid in a cooling bath over a period of about one hour with stirring and air sparging. The air purging was continued for a further hour after the addition of the monomer. 0.084 g of p-methoxyphenol was then added to the mixture as a polymerization inhibitor. The mixture was slowly added to a mixture of 27.6 g (0.2 mol) potassium carbonate, 120 g of ice and 40 ml of distilled water. The pH of the mixture was adjusted to about 7 by the addition of further potassium carbonate. The mixture was filtered and a further 0.08 g of p-methoxyphenol added.

The product formed using higher reaction temperatures separated into two distinct immiscible phases. The impurity was mainly ethylene glycol dimethacrylate and was removed by ether extraction. The aqueous phase was freeze dried and the resultant white powder analysed by $^1$H N.M.R. to give the relative amounts of 2-sulphatoethyl methacrylate, unreacted hydroxyethyl methacrylate and hydrogen chloride addition product.

The results given in Table 1 show the relative amounts, on a molar basis, of the three main products at the different reaction temperatures. The amount of ethylene glycol dimethylacrylate is also given as a mole percentage of the maximum theoretical amount. The temperature is given as the temperature of the cooling bath. The actual reaction temperature would be a few degrees higher. The results show that more of the required product and less by-products are formed by maintaining the temperature below ambient temperature i.e. below 20° C.

TABLE 1

| Bath. Temp (°C.) | Proportions of product on a molar basis | | | Ethylene glycol dimethyl acrylate (mole %) |
|---|---|---|---|---|
| | 2-sulphatoethyl methacrylate | HCl addition product | Unreacted hydroxyethyl methacrylate | |
| −15 | 82 | 12 | 6 | <1 |
| 2 | 90 | 3 | 7 | <1 |
| 10 | 73 | 20 | 8 | <1 |
| 20 | 67 | 24 | 9 | 3 |
| 34 | 59 | 32 | 9 | 23 |
| 43 | 51 | 40 | 10 | 40 |

EXAMPLE 4

A polystyrene-divinylbenzene sulphonate ion exchange resin sold under the trade name Amberlite IR 120(H) was treated with 5% aqueous potassium hydroxide until no further neutralization was observed. The resin was then transferred to a column, treated with one bed volume of 5% aqueous potassium hydroxide and then washed with distilled water until the washings were of neutral pH.

The acid ester, 2-sulphatoethyl methacrylate prepared by a method similar to that described in Example 1 was neutralized by adding it to an aqueous ammonium solution. The ammonium salt was then passed through the column containing the ion exchange resin. Analysis of the product showed that the potassium salt of 2-sulphatoethyl methacrylate had been formed.

EXAMPLE 5

23.3 g (0.2 mol) of chlorosulphonic acid was placed in a flask and cooled in an ice bath to about 5° C. with stirring and air sparging. 26.5 g (0.204 mol) of 2-hydroxyethyl methacrylate were added dropwise over a period of about 2 hours, maintaining the temperature below 10° C. The acid ester product was neutralized by adding it dropwise over a period of about 20 minutes to a mixture of 31.2 g (0.1 mol) barium hydroxide, 60 g ice, 20 ml distilled water. The mixture also contained 0.08 g p-methoxyphenol as polymerization inhibitor. The mixture was purged with air throughout the neutralization and the temperature was maintained below 5° C. The pH of the solution was then adjusted to about 7 by the addition of further barium hydroxide. Insoluble material was removed by filtration and the solution was extracted with heptane to remove dimethacrylate. The solution was freeze dried to give 36.3 g of the barium salt.

EXAMPLE 6

Example 5 was repeated except that 10 g (0.1 mol) of calcium carbonate was used in place of the barium hydroxide in the neutralization of the acid ester and calcium carbonate was used to adjust the final pH of the solution to about 7. 18.1 g of the calcium salt was obtained by freeze drying the solution.

We claim:

1. A method for producing polymerizable monomers having the general formula:

$$CH_2=\overset{R_1}{\underset{|}{C}}-COOR_2SO_3H$$

wherein
$R_1$ is a hydrogen atom or a methyl group
$R_2$ is one or more alkoxylate groups each of which alkoxylate group has from one to four carbon atoms, which method comprises the addition of a hydroxy alkyl acrylate or methacrylate having the formula:

$$CH_2=\overset{R_1}{\underset{|}{C}}-COOR_2H$$

where $R_1$ and $R_2$ are the same as defined above, to chlorosulphonic acid wherein the reaction is carried out at a temperature in the range 0° to 10° C. and in which the reaction mixture is purged with a sparging gas.

2. A method as claimed in claim 1 in which the sparging gas is an oxygen containing gas.

3. A method as claimed in claim 1 in which the hydroxy alkyl acrylate or methacrylate is 2-hydroxyethyl methacrylate.

4. A method for producing polymerizable monomers having the general formula;

$$\left[CH_2=\overset{R_1}{\underset{|}{C}}-COOR_2SO_3\right]_x M$$

where
$R_1$ is a hydrogen atom or a methyl group,
$R_2$ is one or more alkoxylate groups each of which alkoxylate group has from one to four carbon atoms,
M is a metal ion, an ammonium ion or a quaternary ammonium ion and
X is an integer equal to the valency of M, which method comprises neutralizing a polymerizable monomer produced according to the method of claim 1 by reacting the monomer with a basic salt.

5. A method as claimed in claim 4 in which the polymerizable monomer is neutralized with a basic salt of an alkali metal, an alkaline-earth metal, aluminum or iron.

6. A method as claimed in claim 4 in which the polymerizable monomer is neutralized with a sodium or potassium salt.

7. A method as claimed in claim 4 in which the salt is potassium carbonate.

8. A method as claimed in claim 4 in which the monomer is neutralized in the presence of a polymerization inhibitor.

9. A method as claimed in claim 4 in which the reaction mixture is sparged with an oxygen containing gas during the neutralization of the monomer.

10. A method as claimed in claim 4 in which the neutralization of the monomer is carried out at a temperature of less than 20° C.

* * * * *

UNITED STATES PATENT AND TRADEMARK OFFICE
CERTIFICATE OF CORRECTION

PATENT NO. : 4,788,314
DATED : November 29, 1988
INVENTOR(S) : John Naysmith Hay and Ian Grieg Meldrum It is certified that error appears in the above-identified patent and that said Letters Patent is hereby corrected as shown below:

Column 3, line 23, "hydroxyalky" should read --hydroxy alkyl--.

Signed and Sealed this

Eighth Day of August, 1989

Attest:

DONALD J. QUIGG

Attesting Officer

Commissioner of Patents and Trademarks